US00PP33805P2

(12) United States Plant Patent
Danziger

(10) Patent No.: US PP33,805 P2
(45) Date of Patent: Jan. 4, 2022

(54) ***CARYOPTERIS* 'DCARBEYBAR'**

(50) Latin Name: *Caryopteris incana*
Varietal Denomination: DCARBEYBAR

(71) Applicant: Danziger 'DAN' Flower Farm, Beit Dagan (IL)

(72) Inventor: Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

(21) Appl. No.: 17/109,571

(22) Filed: Dec. 2, 2020

(51) Int. Cl.
*A01H 6/50* (2018.01)
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Cassandra Bright

(57) ABSTRACT

A new and distinct variety of *Caryopteris* plant named 'DCARBEYBAR' is disclosed, characterized by tight, dense growth and rich pink flowers. Plants are well suited to container culture. The new variety is a *Caryopteris*, normally used for ornamental horticulture purposes.

3 Drawing Sheets

Latin name of the genus and species: *Caryopteris incana.*
Variety denomination: 'DCARBEYBAR'.

BACKGROUND OF THE INVENTION

The new *Caryopteris* cultivar is a product of chance discovery. The new variety was discovered as a naturally occurring whole plant mutation at a research greenhouse in Moshav Mishmar Hashiva, Israel. The interesting whole plant mutation was discovered during the Fall of 2015.

The parent variety is the unpatented, proprietary variety referred to as *Caryopteris* 'CT-13-163'.

Asexual reproduction of the new cultivar has been performed by terminal vegetative cuttings. This was first performed at a research greenhouse in Moshav Mishmar Hashiva, Israel during 2016 and has shown that the unique features of this cultivar are stable and reproduced true to type in more successive generations.

SUMMARY OF THE INVENTION

The cultivar 'DCARBEYBAR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCARBEYBAR' These characteristics in combination distinguish 'DCARBEYBAR' as a new and distinct *Caryopteris* cultivar:

1. Rich pink flower color.
2. Attractive, tight, dense plant habit.
3. Very good performance as a container plant.

Plants of the new cultivar 'DCARBEYBAR' are similar to plants of the parent, *Caryopteris* 'CT-13-163' in most horticultural characteristics, however, plants of the new cultivar 'DCARBEYBAR' differ in the following;

1. The new variety has a darker immature petal color near Red-Purple 62A, the parent has an immature petal color close to 65B.

2. The new variety has a darker mature petal color near Red-Purple 65C, the parent has an immature petal color close to White N155B.
3. The new variety has longer petals then the parent.

COMMERCIAL COMPARISON

Plants of the new cultivar 'DCARBEYBAR' are comparable to the unpatented commercial variety *Caryopteris* 'Pavillion Pink'. The two *Caryopteris* varieties are similar in most horticultural characteristics; however, the new variety 'DCARBEYBAR' differs in the following:

1. The new variety has darker pink flowers than this comparator.
2. The new variety has single flowers; this comparator has semi-double flowers.

Plants of the new cultivar 'DCARBEYBAR' can also be compared to the unpatented commercial variety *Caryopteris* 'Pink Perfection'. The two *Caryopteris* varieties are similar in most horticultural characteristics; however, the new variety 'DCARBEYBAR' differs in the following:

1. Plants of the new variety are denser, with more branches.
2. Inflorescences of the new variety are denser, with more flowers per inflorescence.
3. Foliage of the new variety is green; foliage of this comparator is grey-green.
4. Foliage of the new variety is much wider than foliage of this comparator.

BRIEF DESCRIPTION OF THE PHOTOGRAPHS

The accompanying photograph in FIG. 1 illustrates in full color a typical flowering plant of 'DCARBEYBAR' grown in a polyhouse in Grand Haven, Mich. Age of the plant photographed is approximately 2 years old from a rooted cutting.

Figure 1:
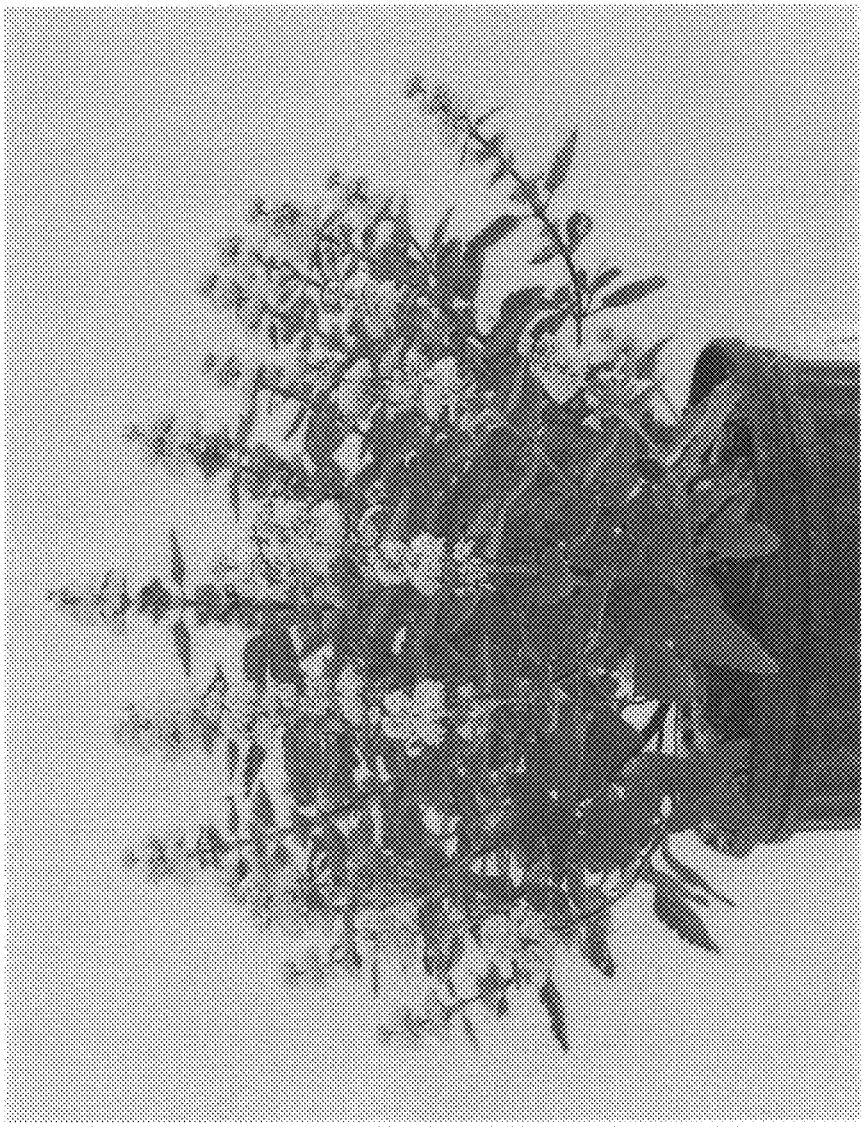
Figure 2:
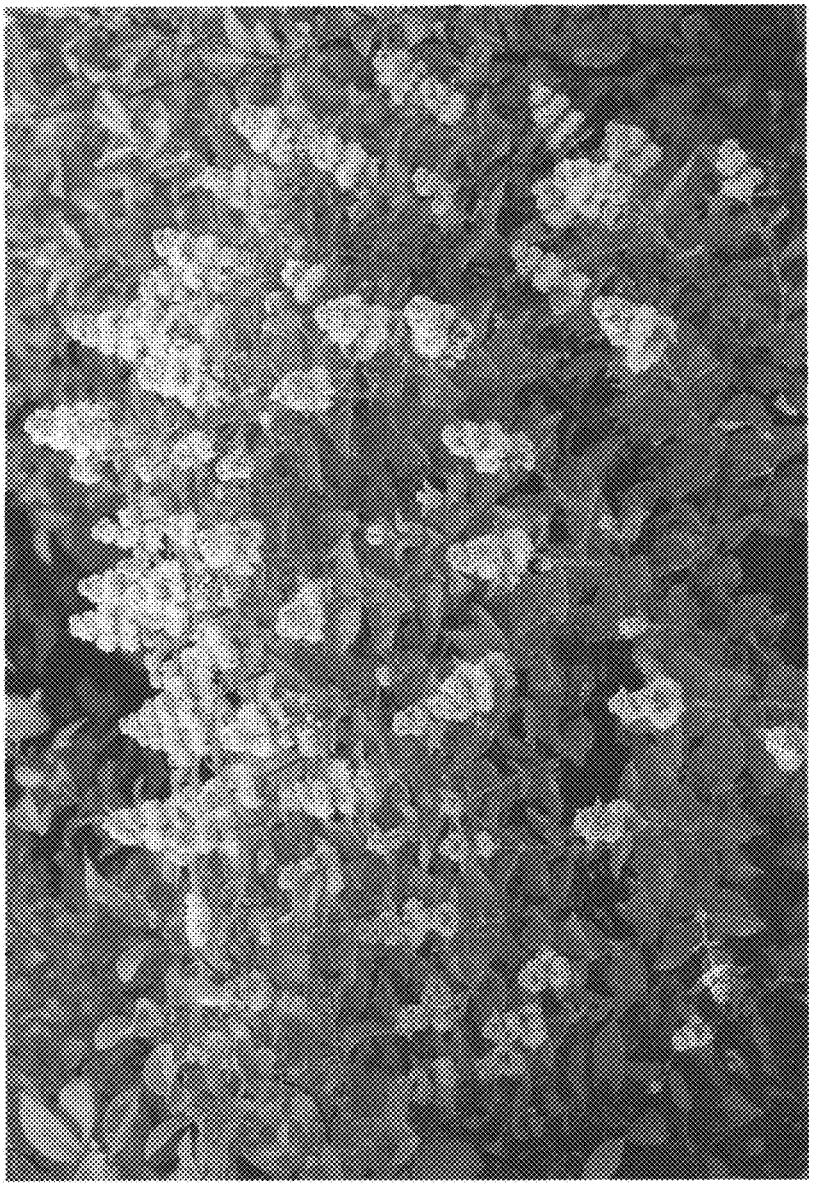
FIG. 2 illustrates a field grown flowering plant of the new variety in Grand Haven, Mich. at about 2 years of age.
Figure 3:
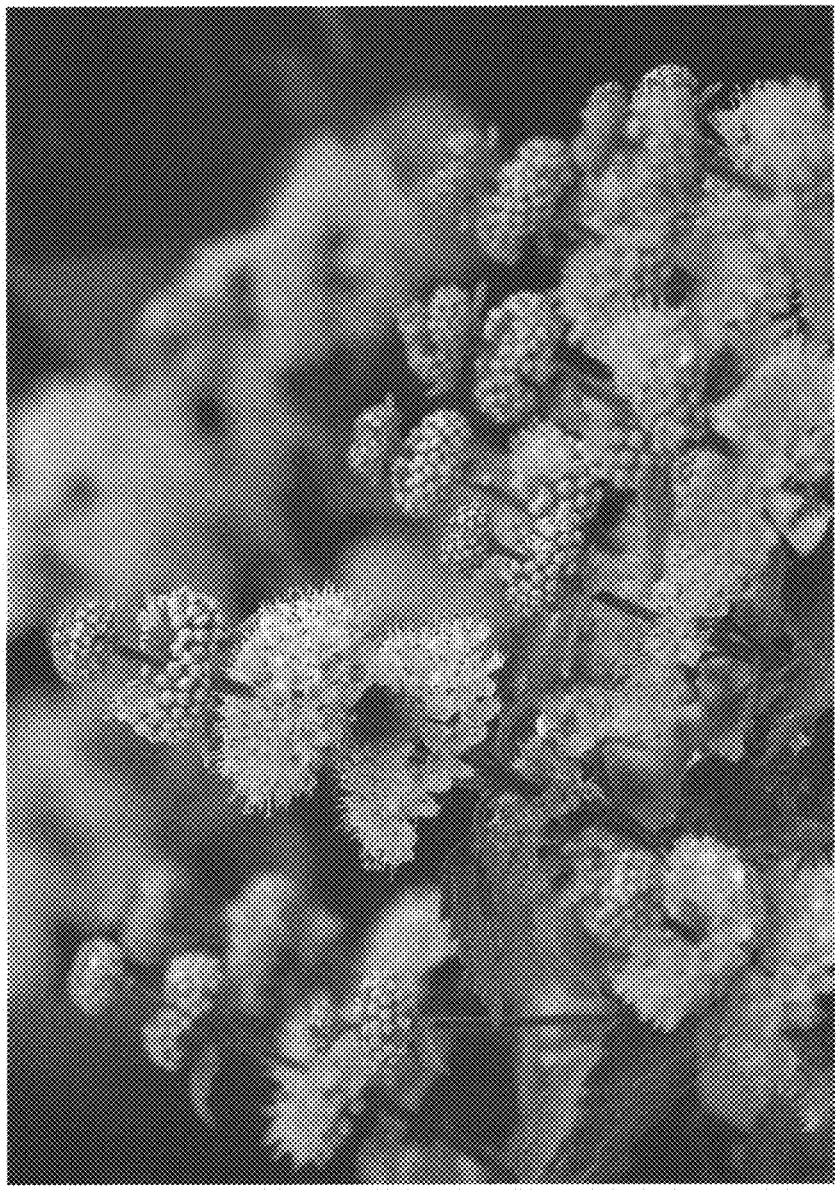
FIG. 3 illustrates a close up of flowers and flower buds.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'DCARBEYBAR' plants grown in a poly house during July of 2017 in Grand Haven, Mich. The growing temperature ranged from approximately 18° C. to 27° C. during the day and from approximately 5° C. to 10° C. during the night. General light conditions are normal sunlight and numerical values represent averages of typical plant types. Measurements were taken during the Summer of 2020.

Botanical classification: *Caryopteris incana* 'DCARBEYBAR'.

PROPAGATION

Type of propagation typically used: Vegetative terminal cuttings.

Time to initiate roots: About 7 days at 20-25° C.

Time to produce a rooted cutting or liner: About 15-20 days at 20-25° C.

Root description: Fibrous system.

PLANT

Type: Flowering perennial shrub.

Age of plant described: Approximately 2 years from rooted cutting, planted in a 3 gallon pot.

Overall plant shape or growth habit: Upright and somewhat outwardly growing.

Plant spread: About 39 cm.

Plant height: Approximately 42 cm.

Growth rate: Moderate.

Length of primary lateral branches: Approximately 35 cm.

Diameter of lateral branches: About 5 mm.

Angle: Acute angle, less than 45 degrees from center of plant.

Quantity of lateral branches: About 15 branches.

- *Color*.—Near Green 143C.
- *Texture*.—Pubescent.
- *Shape*.—Oval to rectangular.

Internode length: Approximately 1.5 cm to 1.75 cm.

FOLIAGE

Leaf:

- *Arrangement*.—Opposite, single.
- *Quantity*.—Approximately 22 per main branch.
- *Average length*.—Approximately 4 cm.
- *Average width*.—Approximately 2.5 cm.
- *Shape of blade*.—Deltoid.
- *Apex*.—Acute.
- *Base*.—Obtuse.
- *Attachment*.—Petiolate.
- *Margin*.—Crenate.
- *Texture of top surface*.—Soft, velvety.
- *Texture of bottom surface*.—Soft, velvety.
- *Color*.—Young foliage upper side: Near Green N137A. Young foliage under side: Near Yellow-Green 147B. Mature foliage upper side: Near Green N137A. Mature foliage under side: Near Yellow-Green 147B.
- *Venation*.—Type: Pinnate. Venation color upper side: Near Yellow-Green 148B. Venation color under side: Near Yellow-Green 145B.
- *Petiole*.—Average Length: Approximately 7.5 mm. Diameter: Approximately 2 mm. Texture: Softly pubescent. Color: Upper: Near Brown 200D. Under: Near Greyed-Green 194A lightly flushed Brown 200D.

FLOWER

Natural flowering season: Late Summer.

Inflorescence type and habit: Axillary cymes composed of single flowers.

Flower longevity on plant: Approximately 7 days.

Quantity of flowers: About 6-12 blooming spikes per each stem at the same time.

Inflorescence size:

- *Height*.—Approximately 3.4 cm.
- *Diameter*.—Approximately 2.5 cm.
- *Flowers and buds per inflorescence*.—About 100 flowers and 100 buds.

Individual flowers:

- *Petal arrangement*.—Zygomorphic with bilabiate petal.
- *Arrangement*.—Simple.
- *Size*.—Diameter: Approximately 0.4 cm. Length: Approximately 0.4 cm.
- *Persistence*.—Self-Cleaning.
- *Fragrance*.—None.

Petals:

- *Quantity*.—5.
- *Shape*.—Obovate, with deep dentations/spurs at apex.
- *Margin*.—Entire.
- *Apex shape*.—Emarginate and spurred/deeply dentate.
- *Length*.—About 4 mm. Tube: About 2 mm. Lower lip: 0.2 cm. Tube: About 1 mm.
- *Texture*.—Glabrous. Tube: Glabrous.

Color: Upper Lip:

- *When opening*.—Inner surface: Near Red-Purple 62A. Outer surface: Near Purple 75C.
- *Fully opened*.—Inner surface: Near Red-Purple 65C. Outer surface: Near Purple 75C.
- *Fading*.—Inner surface: Near Purple 75C. Outer surface: Near Purple 75C.

Color: Lower Lip:

- *When opening*.—Inner surface: Near Red-Purple 62A. Outer surface: Near Purple 75C.
- *Fully opened*.—Inner surface: Near Red-Purple 65C. Outer surface: Near Purple 75C.
- *Fading*.—Inner surface: Near Purple 75C. Outer surface: Near Purple 75C.

Color: Tube:

- *When opening*.—Inner surface: Near Red-Purple 62A. Outer surface: Near Red-Purple 62A.
- *Fully opened*.—Inner surface: Near Red-Purple 62C. Outer surface: Near Red-Purple 62C.
- *Fading*.—Inner surface: Near Purple 75C. Outer surface: Near Purple 75C.

Bud:

- *Shape*.—Spherical.
- *Length*.—Approx. 0.2 cm.
- *Diameter*.—Approx. 0.2 cm.
- *Color*.—Near Red-Purple 62A.

Sepals:
*Shape*.—Linear.
*Quantity per flower*.—5.
*Length*.—Approximately 0.2 cm.
*Width*.—Approximately 0.1 cm.
*Margin*.—Entire.
*Texture*.—Pubescent.
*Color*.—Near Yellow-Green 144C.

Peduncle:
*Length*.—1.5 cm.
*Diameter*.—0.2 cm.
*Texture*.—Softly pubescent.
*Color*.—Near Yellow-Green 144D heavily flushed Greyed-Purple 186A and 186B.
*Angle*.—Upright, about 30 degrees from center.
*Strength*.—Very elastic and strong.

Pedicel:
*Length*.—3 mm.
*Diameter*.—1 mm.
*Texture*.—Softly pubescent.
*Color*.—Near Yellow-Green 144D heavily flushed 186B.
*Angle*.—About 45 degrees.
*Strength*.—Strong, not easily broken.

REPRODUCTIVE ORGANS

Stamens:
*Number*.—5 per flower.
*Filament length*.—Approximately 0.6 cm.

Anthers:
*Shape*.—Round.
*Length*.—About 1 mm.
*Color*.—Near Greyed-Purple 186D.
*Pollen*.—Color: Near White N155B. Quantity: Scant.

Pistil:
*Number*.—1 per flower.
*Length*.—Approximately 1 cm.
*Style*.—Length: Approximately 0.9 cm. Color: Near White N155B.
*Stigma*.—Shape: Linear. Color: Near White N155B. Ovary color: Near Yellow-Green 144B.

OTHER CHARACTERISTICS

Fruits and seeds: Not observed to date.

Disease/pest resistance: Neither resistance nor susceptibility to normal diseases of *Caryopteris*. Typical pathogens include *Prodenia* and *Botrytis*. Typical pests include various Aphid and mite species.

Temperature tolerance: −26° C. lowest temperature tolerant, likely to tolerate colder. Highest temperature tolerant to 35° to 40° C.

Garden performance: Low maintenance, needs well drained soil.

What is claimed is:

1. A new and distinct cultivar of *Caryopteris* plant named 'DCARBEYBAR' as herein illustrated and described.

* * * * *